United States Patent [19]

Mosior

[11] Patent Number: 5,211,303
[45] Date of Patent: May 18, 1993

[54] DUAL CONTAINER SYSTEM WITH SELECTIVE LOCKING FEATURE

[75] Inventor: Donald J. Mosior, Lake Geneva, Wis.

[73] Assignee: Sage Products, Inc., Crystal Lake, Ill.

[21] Appl. No.: 821,012

[22] Filed: Jan. 15, 1992

[51] Int. Cl.⁵ .......................................... B65D 21/02
[52] U.S. Cl. ................................. 220/23.83; 220/23.4; 220/476; 206/465; 206/468; 312/109
[58] Field of Search ..................... 220/476, 23.4, 23.6, 220/23.83; 206/464, 465, 468, 501; 312/109, 107

[56] References Cited

U.S. PATENT DOCUMENTS

| | | | |
|---|---|---|---|
| 3,647,105 | 3/1972 | Keeslar | 220/23.4 |
| 3,701,079 | 10/1972 | Bowden et al. | 220/23.4 |
| 3,763,980 | 10/1973 | Vom Stein et al. | 220/23.4 |
| 3,851,936 | 12/1974 | Muller | 220/23.4 |
| 4,306,655 | 12/1981 | Smith | 220/23.4 |
| 4,717,024 | 1/1988 | Djezovic | 220/23.4 |
| 4,863,057 | 9/1989 | Hanifl | 220/23.4 |

Primary Examiner—Joseph Man-Fu Moy
Attorney, Agent, or Firm—Lee, Mann, Smith, McWilliams, Sweeney & Ohlson

[57] ABSTRACT

A secure container system comprising a first container with a second container mounted thereon, the containers having adjacent sides that are complementary to one another. The first container includes two pairs of spaced channels and the second container includes opposite flanges which engage the channels for mounting the second container on the first. The first container has a door which, when closed, includes an extended portion comprising a stop for selectively preventing lateral movement of the second container relative to the first container when the second container is mounted in only one of the two pairs of spaced channels. The door also includes a pair of detents for temporarily holding the second container relative to the first container when the second container is mounted in a second of the two pairs of spaced channels.

20 Claims, 2 Drawing Sheets

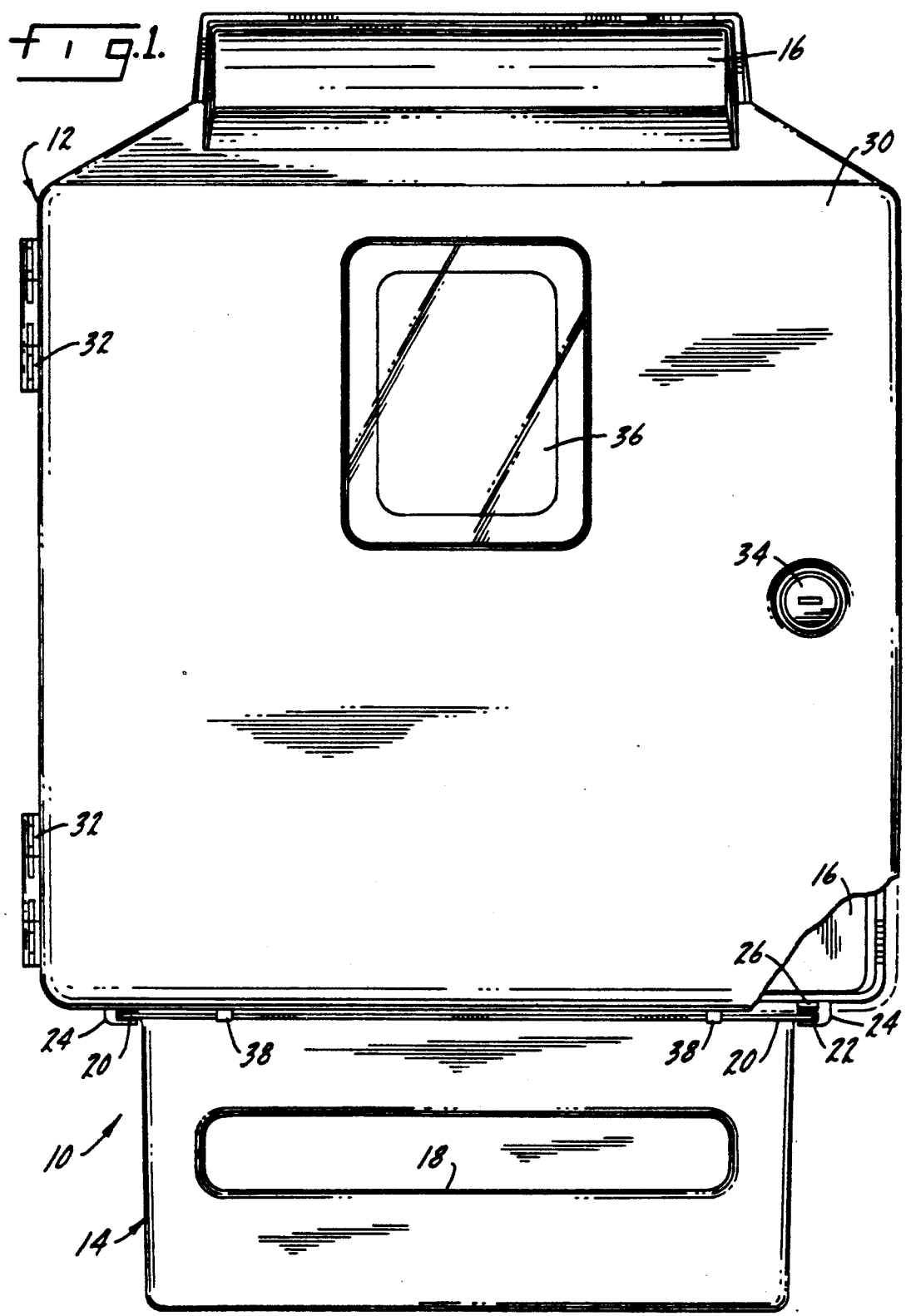

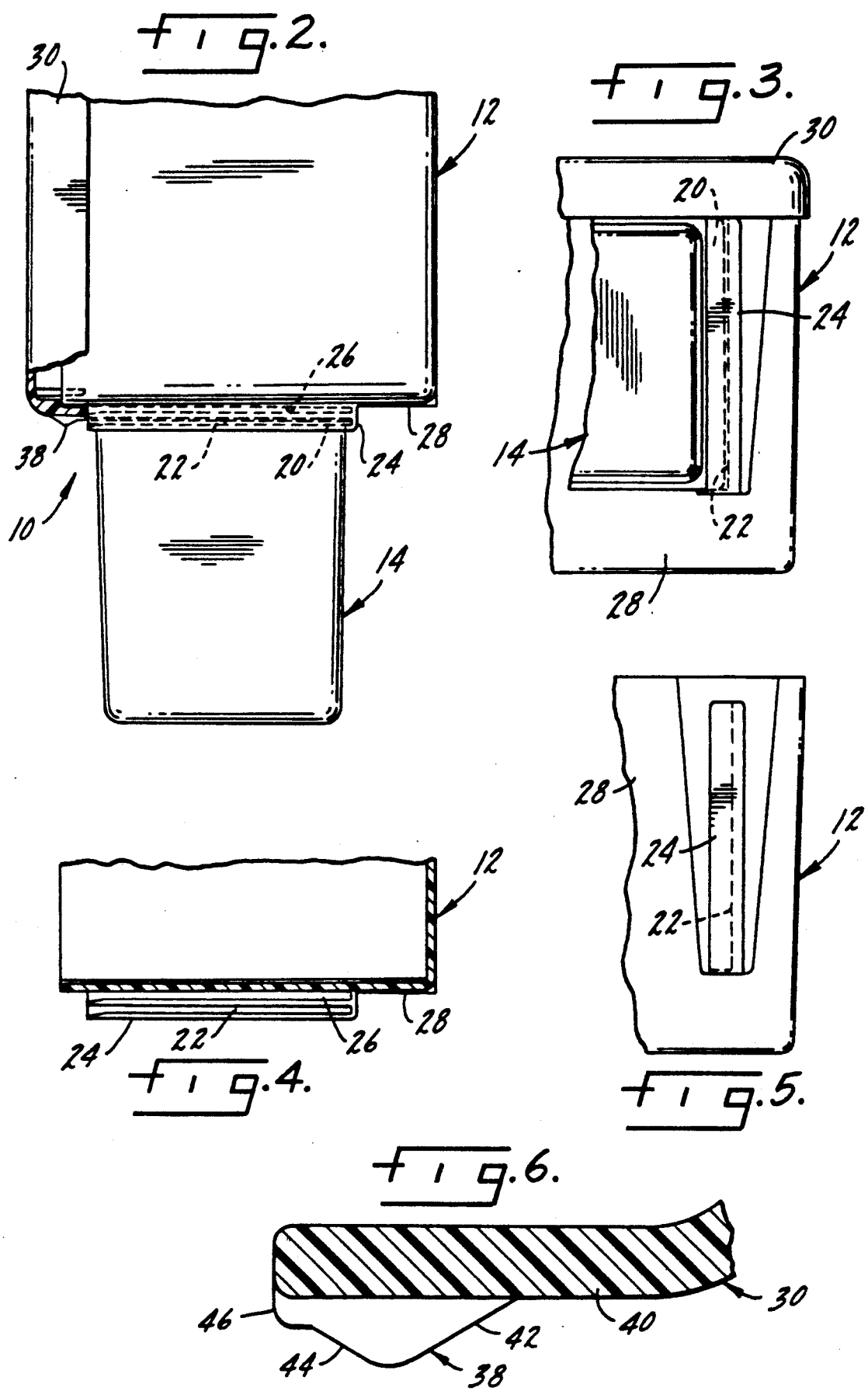

DUAL CONTAINER SYSTEM WITH SELECTIVE LOCKING FEATURE

BACKGROUND OF THE INVENTION

This invention relates to multiple container systems, and in particular to a container system having a second container removably mounted on a first container, with the first container being provided with means for both temporarily locking the second container to the first, and means for simply mounting the second container on the first without the ability to lock the two containers together.

Cleanliness and safety are constant concerns in any medical environment. As a result, disposable, one-time use products have proliferated to the extent that their proper dissemination and disposal have become major concerns in any medical facility. Typically, disposable products, such as sharps, tissues and gloves, are stored on shelves or in cabinets, and when used, are disposed of in wastebaskets or other portable containers which are strategically placed within a room. Dispensing and disposal of such products in secure containers has, until recently, received little consideration.

In U.S. Pat. No. 4,863,057, which is assigned to the same assignee as the present application, there is disclosed a secure container system which can be mounted on a wall and which is used for both dispensing and disposal of disposable products. In that container system, however, when the first container has been closed and locked in place, the second container is always held in place and cannot be removed without opening of the first container. While in some instances that result is desired, in other instances, it is desired to be able to remove the second container without having to unlock and open the first container.

SUMMARY OF THE INVENTION

The invention relates to a secure container system intended to be mounted on the wall in a room within a hospital, clinic, medical office or other medical facility. It is composed of two containers, the second of which is mounted on the first such that the second can be laterally removed from the first when desired. A stop is provided on the first container for selectively preventing removal of the second container if the second container is located in a first mounting position. The stop is positionable in a first orientation to lock the second container in place in the first mounting position and in a second orientation to unlock the second container to permit its removal.

For mounting of the second container on the first, the second container includes opposite flanges extending outwardly from opposite edges of the container. Two pairs of spaced, parallel channels are located on the first container, with each of the channels of each of the pairs of channels being shaped and located to accommodate one of the flanges of the second container. The channels of the first mounting position are located closer to one side of the first container than the channels of the second mounting position so that the stop, when positioned in the first orientation, will lock the second container to the first container only when the second container is located in the first mounting position. It is preferred that the channels of the first and second mounting positions are juxtaposed in brackets extending from the first container.

The first container includes a door oriented generally perpendicular to the mounting location of the second container on the first. The door has an extended portion projecting adjacent the first mounting position, with that extended portion comprising the stop that may selectively prevent or permit removal of the second container from the first mounting position. The door is provided with a lock so that when the door is closed and latched and the second container is located in the first mounting position, the two containers are irremovably secured together.

The door may further include means extending from the extended portion for temporarily holding the second container when mounted in the second mounting position. The means for temporarily holding preferably comprises a pair of spaced detents extending from the bottom of the door and engaging the top of the second container when mounted in the second mounting position so that the container is held in place while dispensing of gloves or other items therefrom, but can be removed against the holding force of the detents when desired and without opening of the door.

BRIEF DESCRIPTION OF THE DRAWINGS

The invention is described in greater detail in the following description of an example embodying the best mode of the invention, taken in conjunction with the drawing figures, in which:

FIG. 1 is a front elevational view of the container system according to the invention with a portion of the first container broken away to illustrate detail, FIG. 2 is a side elevational view of the two containers, with the majority of the upper portion of the first container being removed, and again with a portion of the first container being broken away to illustrate detail, FIG. 3 is a partial bottom plan view of the right hand portion of the container system of FIG. 1, FIG. 4 is a somewhat enlarged cross-sectional illustration of a lower portion of the first container according to the invention, with the second container being removed and with the door of the first container being omitted for purposes of clarity, looking to the left in FIG. 1, FIG. 5 is a bottom plan view similar to FIG. 3, but somewhat enlarged and again, similar to FIG. 4, omitting the second container and the door of the first container for purposes of clarity, and FIG. 6 is a greatly enlarged partial cross-sectional view of a bottom portion of the door for the first container, showing detail of the detent.

DESCRIPTION OF AN EXAMPLE EMBODYING THE BEST MODE OF THE INVENTION

A container system according to the invention is illustrated generally at 10 in the drawing figures. The container system 10 is composed of two containers, a first container 12 and a second container 14. As illustrated and described in greater detail below, the second container 14 is mounted on the bottom of the first container 12 and may be laterally removed from the first container when desired.

The first container 12 may be an outer enclosure for a wall-mounted sharps disposal system, as disclosed and described in U.S. Pat. No. Re, 33,413, reissued Oct. 30, 1990, the patent being a reissue of U.S. Pat. No. 4,715,498, issued Dec. 29, 1987. As set forth in that patent, the container 12 is intended to include a second, inner disposable container 16 which, when filled with discarded sharps and other wastes, may be removed from the container 12 and suitably disposed. The inner container 16 of the present invention may be substantially identical to that of the '413 patent, may be similar to that disclosed in U.S. Pat. No. 4,779,728, or may be any suitable inner container fitting within the first container 12.

The second container 14 has an opening or dispensing slot 18 so that any items contained within the container 14 can be readily dispensed. The container 14 is sized appropriately in the illustrated embodiment of the invention to accommodate a box of disposable gloves (not illustrated) which is installed within the container 14 with its own dispensing slot in alignment with the dispensing slot 18. When the supply of gloves within the box is exhausted, the second container 14 is removed from the first container 12, the empty box is discarded, and a new box is substituted in its place. It should be evident that the container 14 may be used for selective distribution of any of a myriad of other items, such as tissues, as well.

The second container 14 includes a pair of opposite flanges 20 extending outwardly from opposite edges of one side (the bottom 28) of the container 14. Each of the flanges 20 is shown engaged within a lower channel 22 of a bracket 24, which also has an upper channel 26. The brackets 24 are mirror images of one another, and the upper channels 26, as a pair, comprise a first mounting position for the second container 14, while the lower channels 22 comprise a second mounting position for the container 14. Each bracket 24 may be an integral portion of the container 12 or each of the brackets 24 may be adhesively or otherwise secured to the bottom 28 of the container 12 by any suitable means.

The container 12 has a front door 30 which is mounted on the container 12 by a pair of hinges 32. When closed in the orientation illustrated in FIGS. 1–3, the door 30 extends beneath the bottom 28 in alignment with the pair of upper channels 26. When the second container 14 is mounted with its flanges 20 situated in the upper channels 26, and when the door 30 is closed in the orientation illustrated in FIGS. 1–3, the door blocks removal of the container 14 from the container 12. The door 30 therefore acts as a stop when the door is closed. When the door is opened, however, the container 14 may readily be removed from its engaged position in the upper channels 26.

When the container 14 is oriented with its flanges 20 in the lower pair of channels 22, however, opening or closing of the door 30 has no affect, as best shown in FIGS. 1 and 2. The lower channels 22 are formed in the brackets 24 such that when the door 30 is closed, the channels 22 are visible and accessible beneath the door. Therefore, the second container 14 can be installed in or removed from the lowered channels 22 without the necessity of opening the door 30.

Extending from the bottom of the door 30 are a pair of detents 38. A detent 38 is best shown in FIG. 6 as it extends from a bottom flange 40 of the door 30.

Each detent 38 includes an inlet ramp 42 and an outlet ramp 44. A heel 46 extends from the outlet ramp 44 to the flange 40. Preferably, the inlet ramp 42 and the outlet ramp 44 are formed at an angle of about 30° to horizontal.

With the door 30 closed in the orientation shown in FIGS. 1–3, and with the second container 14 located in the lower channels 22, the detents 38 serve to temporarily hold the second container 14 in place. Thus, when gloves or other items are pulled from the dispensing slot 18, the second container 14 is blocked by the detents from being inadvertently pulled from its mounting in the lower channels 22. However, since the second container 14 is preferably made of plastic, while the detents 38 interfere with removal of the container 14 from the lower channels 22, the plastic material of the container 14 gives sufficiently so that with a predetermined amount of force, the second container 14 can easily be removed from its location in the lower channels 22 without opening of the door 30. Thus, the detents 38 only temporarily hold the container 14 in place when installed in the lower pair of channels 22, while the door 30 itself prevents the container 14 from being removed all together when the door 30 is closed and the container 14 is located in the upper channels 26.

In the normal preferred orientation of the detents 38, and with the second container 14 being located in the lower channels 22, the top of the second container 14 extends immediately below the heel 46, and therefore engages only the outlet ramp 44 when the door 30 is closed. When the second container 14 is located in the upper channels 26, however, the heel 46 further helps lock the container 14 in place until the door 30 is opened.

The container 12 includes a lock 34 in the door 30 for securing the door 30 in the closed orientation. The lock 34 therefore serves to protect both the contents of the first container 12 and also to prevent removal of the second container 14 when situated in the upper channels 26 by preventing opening of the door 30. As illustrated, the bottom 28 of the container 12 is generally flat, and the top of the container 14 is generally complementary to that configuration so that the two containers 12 and 14 may be joined without interference. The top of the container 14 may be open to readily permit insertion of a box of gloves, tissues or other items, or may be closed or partially closed, depending on the intended usage of the container 14. The door 30 is generally perpendicular to the juncture of the two containers 12 and 14 in order to provide the necessary inhibiting stop to removal from the upper channels 26 when the door 30 is closed.

The door 30 illustrated in FIG. 1 includes a viewing port or window 36 to permit viewing of the contents of the container 16. Obviously, the window 36 forms no part of the present invention, and can be used or omitted, as desired.

Various changes can be made to the invention without departing from the spirit thereof or scope of the following claims.

What is claimed is:

1. A secure container system for mounting on a wall, comprising
   a. a first container including a side having a predetermined exterior configuration,
   b. a second container including a side having an exterior configuration complementary to said predetermined configuration,
   c. means mounting said second container on the exterior of said first container with said sides adjacent one another and with said second container being accessible independent of said first container, said mounting means being formed to permit lateral movement of said second container relative to said first container and including a first mounting position and a second mounting position, and
   d. stop means mounted on said first container in alignment with said first mounting position for selectively preventing lateral movement of said second container relative to said first container only when said second container is mounted in said first mounting position and for permitting lateral movement of said second container relative to said first container when said second container is in said second mounting position, said step means having an extended portion projecting adjacent a portion of said second container and being positionable in a first orientation to lock said second container when in said first mounting position to prevent such lateral movement and a second orientation to unlock said second container to permit such lateral movement.

2. A container system according to claim 1 in which said mounting means comprises opposite flanges extending outwardly from opposite edges of said side of said second container and each mounting position comprising a pair of spaced, parallel channels located on said side of said first container, each of said channels being shaped to accommodate one of said fingers.

3. A container system according to claim 2 in which the channels of said first mounting position are located closer to said side of said first container than the channels of said second mounting position.

4. A container system according to claim 3 in which the channels of said first and second mounting positions are juxtaposed.

5. A container system according to claim 1 in which said first container includes a door oriented generally perpendicular to said side of said first container, and said door includes an extended portion projecting adjacent said first mounting position, said extended portion comprising said stop means.

6. A container system according to claim 5 in which said door includes hinges securing said door to said first container.

7. A container system according to claim 6 in which said side of said first container is generally flat and lies in a first plane, and said hinges lie in a second plane normal to said first plane.

8. A container system according to claim 5 in which said door further includes means extending from said extended portion for temporarily holding said second container when mounted in said second mounting position.

9. A container system according to claim 8 in which said means for temporarily holding comprises a pair of spaced detents extending from the bottom of said door.

10. A secure container system for mounting on a wall, comprising
   a. a first container including a generally flat exterior side,
   b. a second container including an exterior side having a configuration complementary to said flat side,
   c. means mounting said second container on the exterior of said first container with said sides adjacent one another and with said second container being accessible independent of said first container, said mounting means being formed to permit lateral movement of said second container relative to said first container and including a first mounting position and a second mounting position, and
   d. a door secured to said first container and oriented generally perpendicular to said flat side, said door having an extended portion projecting in alignment said first mounting position but not said second mounting position when said door is closed, said extending portion comprising a stop for selectively preventing lateral movement of said second container relative to said first container only when said second container is mounted in said first mounting position and said door is closed with said second container being permitted to move laterally when said second container is mounted in said second mounting position irrespective of orientation of said door.

11. A container system according to claim 10 in which said mounting means comprises opposite flanges extending outwardly from opposite edges of said side of said second container and each mounting position comprising a pair of spaced, parallel channels located on said side of said first container, each of said channels being shaped to accommodate one of said flanges.

12. A container system according to claim 11 in which the channels of said first mounting position are located closer to said side of said first container than the channels of said second mounting position.

13. A container system according to claim 12 in which the channels of said first and second mounting positions are juxtaposed.

14. A container system according to claim 10 in which said door further includes means extending from said extended portion for temporarily holding said second container when mounted in said second mounting position.

15. A container system according to claim 14 in which said means for temporarily holding comprises a pair of spaced detents extending from the bottom of said door.

16. A secure container system for mounting on a wall, comprising:
   a. a first container including a flat exterior side having two pairs of spaced, parallel channels located thereon,
   b. a second container having opposite flanges extending outwardly from opposite edges of one exterior side of said second container, each of said flanges being complementary to and engaging a respective one of said channels of one of said pairs, said two pairs of channels and said flanges comprising a means for mounting said second container on said first container with said second container being independent of said first container and with a first of said pairs comprising a first mounting position and a second of said pairs comprising a second mounting position, and
   c. a door secured to said first container and oriented generally perpendicular to said flat side, said door having an extended portion projecting in alignment with only said first mounting portion when said door is closed, said extended portion comprising a stop for selectively preventing lateral movement of said second container relative to said first container when said second container is mounted in said first mounting position and said door is closed with said second container being permitted to move laterally when said second container is mounted in said second mounting position irrespective of orientation of said door.

17. A container system according to claim 16 in which the pair of channels of said first mounting position are located closer to said flat exterior side of said first container than the pair of channels of said second mounting position.

18. A container system according to claim 17 in which the channels of said first and second mounting positions are juxtaposed.

19. A container system according to claim 16 in which said door further includes means extending from said extended portion for temporarily holding said second container when mounted in said second mounting position.

20. A container system according to claim 19 in which said means for temporarily holding comprises a pair of spaced detents extending from the bottom of said door.

* * * * *